(12) United States Patent
Bohnen et al.

(10) Patent No.: US 6,700,021 B2
(45) Date of Patent: Mar. 2, 2004

(54) PREPARATION OF ALDEHYDES

(75) Inventors: Hans Bohnen, Moers (DE); Carl Dieter Frohning, Wesel (DE); Ernst Wiebus, Oberhausen (DE)

(73) Assignee: Celanese Chemicals Europe GmbH (DE)

( * ) Notice: Subject to any disclaimer, the term of this patent is extended or adjusted under 35 U.S.C. 154(b) by 0 days.

(21) Appl. No.: 10/188,986

(22) Filed: Jul. 3, 2002

(65) Prior Publication Data

US 2003/0083528 A1 May 1, 2003

(30) Foreign Application Priority Data

Jul. 7, 2001 (DE) .......................................... 101 33 072

(51) Int. Cl.[7] ............................. C07C 45/49; B01J 23/40
(52) U.S. Cl. ........................ 568/429; 568/454; 502/326
(58) Field of Search ................................ 568/429, 454; 502/326

(56) References Cited

U.S. PATENT DOCUMENTS 5,932,761 A * 8/1999 Omatsu et al.
5,936,130 A * 8/1999 Mori et al.
6,191,063 B1 * 2/2001 Bogdanovic et al.

FOREIGN PATENT DOCUMENTS

| EP | 0246475 | 11/1987 |
| EP | 0544091 | 6/1993 |

* cited by examiner

*Primary Examiner*—Johann Richter
*Assistant Examiner*—Sikarl A. Witherspoon
(74) *Attorney, Agent, or Firm*—Muserlian, Lucas and Mercanti

(57) ABSTRACT

The present invention relates to a process for preparing aldehydes by reaction of olefinically unsaturated compounds with carbon monoxide and hydrogen, wherein, during the process, rhodium is added in the form of a reaction product from the reaction of metallic rhodium and/or more than one rhodium compound with rhodium-complexing compounds and with carbon monoxide and hydrogen, the use of said reaction product in catalytic processes and also the preparation of a catalytic composition with addition of said reaction product.

11 Claims, No Drawings

PREPARATION OF ALDEHYDES

The present invention relates to a process for preparing aldehydes in the presence of a catalyst based on rhodium, wherein, during the process, supplementary rhodium is added to the process in the form of a specific reaction product. The invention further relates to the use of said reaction product and also a process for preparing a catalytic composition by the use of said reaction product.

It is known that aldehydes and alcohols containing one carbon atom more than a starting olefin may be prepared by transition metal-catalyzed reactions of the olefin with carbon monoxide and hydrogen (hydroformylation). In addition to cobalt, which finds industrial use as a catalytic metal on a large scale, rhodium in particular has gained increasing importance in recent years.

In the processes established in the art, the rhodium catalyst is generally a hydridorhodium carbonyl modified by additional ligands, in particular tertiary organic phosphines or phosphites. Usually, the ligands are present in excess so that the catalyst system, which is dissolved in the organic reaction product, comprises complex compounds and free ligand. The use of the rhodium catalysts described enables the hydroformylation reactions to be carried out at pressures below 30 MPa.

The hydroformylation reaction is generally run according to the aldehyde output. After a certain operation time, a loss of activity is observed which is manifested in a reduced aldehyde output. The cause for the loss of activity is believed to be the increased occurrence of catalyst and ligand decomposition products which react with the rhodium catalyst to form complex compounds which only have low catalytic activities, or an increasing concentration of high-boilers in the reaction mixture.

To counteract this loss of activity, EP-A-0544091 suggests the addition of maleic anhydride, fumaric acid or other olefinically unsaturated compounds to a used catalyst solution. These compounds react with the damaging decomposition products to form compounds which apparently no longer impair the activity of the rhodium catalyst. A disadvantage of this process is the very high quantity of maleic anhydride added. This process has therefore hitherto been unable to establish itself in the art.

DE-A1-199 40 249 relates to a process for preparing aldehydes with the use of an aqueous catalyst solution which as well as rhodium and aqueous phosphines comprises salts of aromatic sulfonic, carboxylic or phosphonous acids. The addition of these salts to used hydroformylation catalyst solutions leads to a clear improvement in activity in the hydroformylation reaction. Even the addition of these salts to freshly prepared catalyst solutions has a stabilizing effect and increases the catalyst lifetime. However, this process also requires the addition of supplementary salts to the aqueous catalyst solution which leads to the solubility limits of the ligand and its decomposition products being exceeded more quickly. Shortening of the life cycle of the catalyst solution or the catalyst on-stream time is the consequence.

EP-A-0269964 describes a process for preparing aldehydes, wherein, to maintain the original phosphine concentration, fresh phosphine solution is added until the total concentration of complexing phosphines and non-complexing secondary and decomposition products of the phosphines is about 35 to 45% by weight, based on the aqueous solution.

The industrial operation of the hydroformylation reaction is generally controlled by increasing the temperature with decreasing activity of the catalyst solution, i.e. reduced aldehyde output. However, this measure has the disadvantage of an increased thermal loading of the catalyst system which in turn leads to increased damage of the catalyst.

The inventors found that the aldehyde output may in principle also be increased by, instead of increasing the temperature, making an early supplementary addition of fresh rhodium compounds, e.g. of rhodium acetylacetonate, rhodium carboxylates or inorganic rhodium salts.

The use of a rhodium catalyst which has been preformed, i.e. obtained by a preceding reaction of a rhodium compound with carbon monoxide and hydrogen, as starting catalyst for a hydroformylation is known from EP-A-0246475. In this reference, the use of the preformed catalyst at the start of the hydroformylation reaction serves to reduce the reaction time in the initial phase of the reaction and to prevent the effluence of noble metal in this reaction segment.

Similarly, DE-A1-199 40 249 refers to the possibility of subjecting the rhodium catalyst before use as a starting catalyst in the hydroformylation reaction to a pretreatment in the presence of carbon monoxide and hydrogen.

EP-B1-0 695 734 includes a preforming step as a component of a process for rhodium recovery from the output of the hydroformylation.

However, the previously cited prior art contains no reference to preventing the loss of activity taking place during the hydroformylation process by adding further rhodium, and consequently the cited prior art contains no reference either to the form in which further rhodium may be added for optimal prevention of loss of activity.

It has now been found that the productivity of the hydroformylation reaction can be distinctly improved by rhodium supplementation when rhodium or a rhodium compound is not added untreated to the hydroformylation reactor, but is only added after it has been subjected to a pretreatment using carbon monoxide and hydrogen in the presence of rhodium-complexing compounds.

This is particularly surprising in that the pretreatment actually takes place under the conditions of the hydroformylation reaction ($CO/H_2$ pressure). Those skilled in the art would therefore have expected that a separate, preceding reaction of the supplementarily added rhodium or rhodium compound with carbon monoxide and hydrogen under pressure would be superfluous because such a reaction would actually also take place in the hydroformylation reactor under similar conditions. However, this expectation was very surprisingly incorrect. Apparently, under the conditions of the ongoing hydroformylation, a portion of the supplementarily added rhodium or rhodium compound is not converted to the active species. If, however, the rhodium or rhodium compound is first subjected to a separate pretreatment step in the presence of rhodium-complexing compounds with carbon monoxide and hydrogen, the reaction product generated is able to exhibit its activity in the ongoing hydroformylation losslessly, as it were. The present invention is therefore able to enormously increase the efficiency of the hydroformylation in relation to the rhodium used.

Without wishing to be bound to this theory, it is believed that a rhodium compound pretreated in this way appears to be present in such a form that it does not enter into competing reactions with ligand degradation products of the rhodium catalyst but is able to fully exhibit its catalytic activity.

It is therefore an object of the invention to provide a process for preparing aldehydes by the reaction of olefinically unsaturated compounds with carbon monoxide and hydrogen (referred to in the following as hydroformylation processes), which may also be operated over a relatively long period of time with high activity and without an increase in the reactor temperature which accompanies increased catalyst degradation or the addition of large quantities of extraneous additional compounds which increase the activity of the catalyst being necessary, and wherein the rhodium used is utilized optimally.

The invention therefore provides a process for preparing aldehydes by reaction of olefinically unsaturated compounds with carbon monoxide and hydrogen at temperatures of from 20 to 200° C. and pressures of from 0.1 to 50 MPa in the liquid phase in the presence of a catalyst based on rhodium, which comprises, during the process, adding supplementary rhodium in the form of a reaction product prepared by reacting metallic rhodium and/or one or more rhodium compounds in the presence of rhodium-complexing compounds with carbon monoxide and hydrogen.

In the process for preparing aldehydes, olefinically unsaturated compounds, preferably having from 3 to 20 carbon atoms, are reacted with carbon monoxide and hydrogen at a temperature of from 20 to 200° C., preferably from 40 to 150° C., and a pressure of from 0.1 to 50 MPa, preferably from 1 to 20 MPa, in the presence of a catalyst based on rhodium. The reaction is preferably carried out in the additional presence of phosphorus compounds which generally function as ligands in the catalyst system.

The rhodium-complexing compounds are conveniently such compounds as are also used as ligands in the hydroformylation reaction. Therefore, phosphorus compounds in particular are useful rhodium-complexing compounds.

The conditions of the hydroformylation reaction are known per se and reference may be made, for example, to the prior art mentioned in the introduction.

The olefinically unsaturated compound may contain one or more than one carbon—carbon double bond. The carbon—carbon double bond may be terminal or internal (internal olefins). Preference is given to olefinic compounds having terminal carbon—carbon double bonds.

Examples of α-olefinic compounds (having terminal carbon—carbon double bonds) are alkenes, alkylene alkanoates, alkylene alkyl ethers and alkenols, in particular those having from 3 to 12 carbon atoms. Without claiming comprehensiveness, useful α-olefinic compounds include propylene, 1-butene, 1-pentene, 1-hexene, 1-heptene, 1-octene, 1-decene, 1-dodecene, 1-octadecene, 2-ethyl-1-hexene, styrene, 3-phenyl-1-propene, allyl chloride, 1,4-hexadiene, 1,3-butadiene, 1,7-octadiene, 3-cyclohexyl-1-butene, hex-1-en-4-ol, oct-1-en-4-ol, vinylcyclohexene, n-propyl 7-octenoate, 7-octenoic acid and 5-hexenamide.

Examples of further suitable olefinic compounds include butene-2, diisobutylene, tripropylene, raffinate II (mixture of 1-butene, 2-butene and butane), Octol or Dimersol (dimerization products of butenes), tetrapropylene, cyclohexene, dicyclopentadiene, acyclic, cyclic or bicyclic terpenes, such as myrcene, limonene and pinene. The hydroformylation is preferably carried out using olefinic compounds having from 3 to 12 carbon atoms.

The preparation of the aldehydes may be carried out in the liquid phase monophasically in an organic phase (homogeneous process) or biphasically in the presence of an organic and an aqueous phase (heterogeneous process). The conversion of the olefins is preferably carried out according to the heterogeneous process in the presence of an organic and an aqueous phase.

The preparation of the aldehydes is generally carried out in the presence of organophosphorus compounds or their salts.

The organophosphorus compounds are conveniently chosen according to the type of the hydroformylation process. When the hydroformylation is carried out homogeneously and monophasically in organic solvents, it is convenient to use organophosphorus compounds which are water-insoluble, i.e. are soluble in organic solvents.

The term "homogeneous reaction system" refers to a homogeneous solution which is substantially composed of solvent, catalyst, olefinically unsaturated compound and reaction product, wherein the catalyst comprises rhodium and the organophosphorus compound (complexed or uncomplexed). Rhodium is generally present as a rhodium complex compound which comprises the organophosphorus compounds as the ligands. Such complex compounds and their preparation are known (cf. e.g. U.S. Pat. No. 3,527,809, U.S. Pat. No. 4,148,830, U.S. Pat. No. 4,247,486, U.S. Pat. No. 4,283,562). They may be used as unitary complex compound or else as mixtures of different complex compounds. The rhodium concentration in the reaction medium extends over a range from about 1 to about 1000 ppm by weight and is preferably from 10 to 700 ppm by weight. Rhodium is used in particular in concentrations of from 25 to 500 ppm by weight, based in each case on the homogeneous reaction mixture. A useful catalyst may be a stoichiometrically composed rhodium complex compound. However, it has proven to be convenient to carry out the hydroformylation in the presence of a catalyst system comprising a rhodium-phosphorus complex compound and free, i.e. excess, phosphorus ligand which does not enter into complex formation with rhodium. The free phosphorus ligand may be the same as in the rhodium complex compound, but other ligands may also be used. The free ligand may comprise a unitary compound or a mixture of different organophosphorus compounds. Examples of preferred organophosphorus compounds in the rhodium complex catalysts for the homogeneous process include triarylphosphines such as triphenylphosphine, trialkylphosphines such as tri(n-octyl)phosphine, trilaurylphosphine, tri(cyclohexyl)phosphine, alkylphenylphosphines, cycloalkylphenylphosphines, organic diphosphines and organic diphosphites. Owing to its easy availability, triphenylphosphine is used particularly frequently. Customarily, the molar ratio of rhodium to phosphorus is from 1:1 to 1:300, although the molar content of phosphorus in the form of organophosphorus compounds may be even higher. Preference is given to using rhodium and organically bonded phosphorus in molar ratios of from 1:3 to 1:200. The use of triarylphosphines is particularly favorable when Rh/P molar ratios of from 1:50 to 1:150 are used. When trialkylphosphines are used as ligands, the molar ratio of rhodium to phosphorus is from 1:3 to 1:20.

The monophasic hydroformylation is generally carried out in the presence of a solvent. Useful solvents include organic compounds in which the starting material, reaction product and catalyst system are soluble. Examples of such compounds include aromatic hydrocarbons such as benzene, toluene or the xylenes. Other useful solvents include paraffin oil, ketones or ethers. Particularly suitable solvents include the higher-boiling condensation compounds of the aldehydes which are by-produced in the hydroformylation. The content of the solvent in the reaction medium may be varied within a wide concentration range and is customarily from 20 to 90% by weight, preferably from 50 to 80% by weight, based on the reaction mixture.

However, when the hydroformylation is carried out heterogeneously and biphasically in the presence of an aqueous phase, it is convenient to use water-soluble organophosphorus compounds.

Preference is given to carrying out the preparation of the aldehydes according to the heterogeneous biphasic liquid—liquid process in the presence of an aqueous phase which comprises at least one rhodium compound and also at least one organophosphorus compound as the catalyst. The conversion of the olefins by the heterogeneous process is described, e.g. in DE 26 27 354. The process is characterized by the presence of an organic phase which comprises the olefinic starting material and the reaction product and an aqueous phase in which the catalyst is dissolved. Useful catalysts include water-soluble rhodium complex compounds which comprise water-soluble organophosphorus (III) compounds as ligands. Examples of water-soluble phosphorus(III) compounds which form complex compounds with rhodium include triarylphosphines, trialkylphosphines and arylated or alkylated diphosphines whose organic radicals contain sulfonic acid groups or carboxyl groups. Their preparation and use is known, e.g. from DE 26 27 354, EP 0103810, EP 0163234 and EP 0571819. Further groups of suitable compounds include sulfonated or carboxylated organic phosphites and also heterocyclic compounds of trivalent phosphor (cf. e.g. EP 0575785, EP 0640588).

Particular preference is given to using aqueous hydroformylation catalyst systems which comprise rhodium and, complexed and optionally in excess, arylphosphines of the general formula (I)

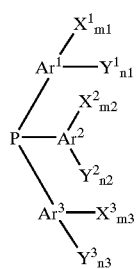

(I)

where $Ar^1$, $Ar^2$ and $Ar^3$ are each a phenyl or naphthyl group, $Y^1$, $Y^2$ and $Y^3$ are each a straight-chain or branched alkyl group having from 1 to 8 carbon atoms, a straight-chain or branched alkoxy group having from 1 to 8 carbon atoms, a halogen atom, an OH, CN, $NO_2$ or $NR^1R^2$ group, where $R^1$ and $R^2$ are each a straight-chain or branched alkyl group having from 1 to 8 carbon atoms, $X^1$, $X^2$ and $X^3$ are each a carboxylate ($COO^-$) and/or a sulfonate ($SO_3^-$) radical, m1, m2 and m3 are identical or different numbers from 0 to 3, where at least one number m1, m2 or m3 is equal to or greater than 1 and n1, n2 and n3 are identical or different integers from 0 to 5.

Examples of these water-soluble organophosphorus compounds include: water-soluble salts of mono-, di- or trisulfonated triphenylphosphine compounds such as trisodium tris(m-sulfonatophenyl)phosphine (TPPTS), dipotassium bis(m-sulfonatophenyl)phenylphosphine dihydrate (TPPDS) and also sodium diphenylphosphinobenzene-3-sulfonate (TPPMS). Particular preference is given to TPPTS.

It is believed that catalytically active rhodium complex compounds which contain carbon monoxide and the arylphosphine of the general formula I as ligands and are dissolved in the aqueous phase form from the water-soluble arylphosphine of the general formula (I) and the rhodium compound used under the conditions of the hydroformylation reaction in the presence of synthesis gas. In general, the aqueous catalyst solution comprises an excess of arylphosphines of the general formula (I) which may also be present as mixtures.

The organic phase consists essentially of the starting olefin and/or the reaction product of the hydroformylation, optionally one or more organic solubilizers and also optionally an organic solvent. Useful cationic solubilizers of the general formula $[A-N(R^3R^4R^5)]^+E^-$ where A is a straight-chain or branched alkyl radical having from 6 to 25 carbon atoms, $R^3$, $R^4$ and $R^5$ are identical or different and are each straight-chain or branched alkyl radicals having from 1 to 4 carbon atoms and E is in particular sulfate, tetrafluoroborate, acetate, methosulfate, benzenesulfonate, alkylbenzenesulfonate, toluenesulfonate, lactate or citrate.

When operation is effected in the presence of a solvent, inert aliphatic compounds are used, such as alkanes, e.g. $C_5$–$C_9$-alkanes such as cyclohexane and n-pentane, or aromatic compounds, such as toluene, xylene, ethylbenzene, mesitylene or chlorobenzene.

The volume ratio of the organic phase to the aqueous catalyst solution is in general from 5:1 to 1:5. Preference is given to a range of from 3:1 to 1:2. A higher proportion of the organic phase generally leads to a slowing of the reaction rate, while a smaller proportion of the organic phase leads to a higher transfer of rhodium into the organic phase.

At the beginning of the hydroformylation reaction, the rhodium is used either as the metal or as a compound. In metallic form, it is used either as finely divided particles or precipitated as a thin layer on a support, such as activated carbon, calcium carbonate, aluminum silicate or alumina. Useful rhodium compounds include salts of aliphatic mono- and polycarboxylic acids, such as rhodium 2-ethylhexanoate, rhodium acetate, rhodium oxalate, rhodium propionate or rhodium malonate. Rhodium salts of inorganic hydro and oxo acids, such as rhodium nitrate or rhodium sulfate, the various rhodium oxides or also rhodium carbonyl compounds such as $Rh_3(CO)_{12}$ or $Rh_6(CO)_{16}$ or complex compounds of rhodium, e.g. cyclooctadienylrhodium compounds or rhodium acetylacetonate may also be used. Rhodium halide compounds are less useful in view of the corrosive nature of the halide ions.

Preference is given to using rhodium oxide and in particular rhodium acetate and rhodium 2-ethylhexanoate.

The rhodium concentration is conveniently from 150 to 800, preferably from 200 to 400 mg of rhodium, based on 1 kilogram of aqueous catalyst phase.

The pH of the aqueous catalyst solution in the biphasic process is generally above 3, preferably in the range from 5 to 8. The use of an aqueous buffer solution to maintain a certain pH value may be necessary. Useful buffer solutions include aqueous solutions of alkali metal or alkaline earth metal salts, such as phosphates, hydrogen phosphates, carbonates, hydrogen carbonates, borates or acetates.

The heterogeneous hydroformylation may also advantageously be carried out when rhodium and arylphosphines are not used in the stoichiometric ratio, i.e. corresponding to the chemical composition of the rhodium complex compound which forms in the course of the preforming or hydroformylation step, but instead the arylphosphines are used in excess. The molar ratio of rhodium to arylphosphine, in particular that of the general formula (I), also expressed as the ratio of rhodium to phosphorus in arylphosphine, may vary within a wide range. In general, about 1 to 5000 mol of phosphorus are used per mole of rhodium. Preference is given to a molar ratio of phosphorus(III) to rhodium of from 1 to 200 and in particular from 50 to 150. The actual hydroformylation catalyst as well as excess arylphosphine are referred to as the catalyst system.

The reaction of the olefins with hydrogen and carbon monoxide (synthesis gas) in the hydroformylation is generally carried out both homogeneously and heterogeneously at a pressure of from 0.1 to 50 MPa, preferably from 1 to 50 MPa, more preferably from 1 to 20 MPa, even more preferably from 2 to 20 MPa and most preferably from 3 to 8 MPa, and at a temperature of from 20 to 200° C., preferably from 40 to 200° C., more preferably from 40 to 150° C., even more preferably from 80 to 150° C. and most preferably from 110 to 130° C. High pressures promote the activity of the catalyst system, but reduce the selectivity ratio of straight-chain aldehyde to branched aldehyde. When the temperature is too low, the reaction rate is unacceptably slow, whereas when the temperature is too high, which, after all, it is to be avoided according to the invention, catalyst damage reaches an unacceptable level. The optimal hydroformylation conditions, in particular the rhodium concentration, the pressure and the temperature, depend upon the olefinic compound to be used. Reactive olefins, such as propylene, butene-1, pentene-1, hexene-1 and butadiene-1,3, only require low rhodium concentrations, low pressures and low temperatures. In contrast, the conversion of less reactive olefinic compounds, e.g. of butene-2 and other olefins having internal double bonds, requires relatively high rhodium concentrations, pressures and temperatures.

The catalyst may also be added preformed to the reaction mixture at the beginning of the hydroformylation (see e.g. EP-A-0246475). To this end, the aqueous solution comprising rhodium, preferably as rhodium 2-ethylhexanoate, and the arylphosphines, preferably of the general formula (I), is first treated with synthesis gas at elevated temperature and elevated pressure over a period of from 0.1 to 10 hours. In general, the conditions of the preformation correspond to those of the actual hydroformylation in the presence of the olefinic compounds to be converted which follows the preforming step.

The composition of the synthesis gas, i.e. the ratio of carbon monoxide to hydrogen may vary within a wide range. In general, synthesis gas is used where the volume ratio of carbon monoxide to hydrogen is about 1:1 or differs only slightly from this ratio. The preformation of the starting catalyst and the hydroformylation are generally carried out using synthesis gas of the same composition.

The hydroformylation may be carried out either batchwise or else continuously. The batchwise method involves freeing the hydroformylation mixture of carbon monoxide and hydrogen by depressurization after the end of the reaction.

After the end of the hydroformylation reaction in the presence of an aqueous phase a liquid organic, aldehydic upper phase and a lower aqueous phase comprising the catalyst are present and may be separated from each other by simple phase separation. After the phase separation, the aqueous catalyst phase, optionally after supplementary addition of fresh catalyst pretreated according to the invention, as described below, is fed back into the hydroformylation process.

The hydroformylation process of the invention involves additional rhodium being added in the form of a reaction product prepared by reacting metallic rhodium and/or one or more rhodium compounds in the presence of rhodium-complexing compounds with carbon monoxide and hydrogen.

The supplementary addition of the rhodium reaction product may take place at any time after the beginning of the hydroformylation reaction. It is advantageous to add it when a loss of activity which manifests itself in a reduced aldehyde output has occurred, or else in good time before such a loss of activity occurs, when this may be anticipated in view of the known on-stream times of the originally used catalyst.

The point in time at which the addition of supplementary rhodium in the form of the reaction product used in accordance with the invention takes place and the quantities of the reaction product which are added in each case are in principle not subject to any restriction. They depend upon the way in which the reactor is operated. For instance, it is possible to begin supplementary addition of rhodium at an early point in time in small quantities and in this way to maintain the conversion at the starting level, or to add a large quantity of rhodium after a longer period of time. For example, when larger quantities of the reaction product are added after a longer period of time, the addition takes place, e.g. from 20 to 30 days after the beginning of the hydroformylation reaction. When smaller quantities of the reaction product are added at shorter intervals, the addition may proceed after only about 4 to 5 days and this addition may be repeated at these intervals.

The addition of the rhodium reaction product is generally carried out such that a solution of the reaction product without workup as obtained from the pretreatment is added directly to the hydroformylation reactor. When the hydroformylation is carried out homogeneously, the organic solution obtained of the reaction product is added. When the hydroformylation is carried out heterogeneously, an aqueous solution of the reaction product is added. In principle, heterogeneous reaction operation also allows the rhodium reaction product to be added to a catalyst-containing phase discharged from the reactor which is then returned to the reactor. However, this is not preferred.

The quantity of the rhodium reaction product which is added in every addition depends as already described on the way in which the reactor is operated. When small quantities are added at short intervals, the quantity of the rhodium reaction product, based on the rhodium in the rhodium reaction product, is at least about 1% by weight, based on the rhodium already present in the reactor. When larger quantities of the rhodium reaction product are added at longer intervals, a maximum of about 30% based on the rhodium already present in the reactor is added per supplementary addition, based on the rhodium in the rhodium reaction product.

The preparation of the rhodium reaction product which is added supplementarily to the ongoing hydroformylation is carried out using metallic rhodium or one or more rhodium compounds.

The above remarks relating to the starting catalyst of the hydroformylation also apply to metallic rhodium.

The preparation of said reaction product may preferably be carried out using one or more rhodium salts. The above remarks relating to the starting catalyst for the hydroformylation also apply to the rhodium salts.

The rhodium salt is more preferably one of an organic compound, of which in turn those selected from the group of rhodium salts consisting of rhodium(III) salts of beta-diketones and rhodium salts of carboxylic acids are more preferred.

The carboxylic acids may be mono- or polybasic, and straight-chain or branched. The salts of saturated or unsaturated aliphatic acids and salts of aromatic acids are suitable. The salts are prepared, e.g. by reaction of aqueous rhodium salt solutions such as rhodium(III) nitrate or rhodium(III) sulfate with the aqueous solutions of salts of the organic acids or by reaction of rhodium oxide or rhodium oxide hydrates with the free acids.

Said reaction product is more preferably prepared by the reaction of one or more rhodium salts selected from the group of rhodium salts consisting of rhodium(III) acetylacetonate and rhodium (preferably rhodium(III)) salts of aliphatic monocarboxylic acids having from 2 to 18, preferably from 2 to 12, more preferably from 2 to 10 carbon atoms, with carbon monoxide and hydrogen.

The rhodium salts of saturated monocarboxylic acids having from 2 to 10 carbon atoms are particularly suitable. Examples of these acids include acetic acid, propionic acid, n-butyric acid, i-butyric acid, pentanoic acid, hexanoic acid and 2-ethylhexanoic acid.

When the hydroformylation is carried out as a biphasic reaction in the presence of an aqueous phase, rhodium acetate (rhodium(III) acetate or rhodium(II) acetate, preferably rhodium(III) acetate) is the most preferred starting material. On the contrary, when the hydroformylation is carried out monophasically in an organic solvent, rhodium (II) 2-ethylhexanoate is the most preferred starting material.

The preparation of said reaction product may in principle be carried out under the pressure and temperature conditions of the hydroformylation.

The composition of the $CO/H_2$ mixture may be varied within a wide range. It is possible to use either carbon monoxide-rich or else hydrogen-rich mixtures. Customarily, mixtures are used in which carbon monoxide and hydrogen are present in approximately the volume ratio 1:1, i.e. a composition as is used in the subsequent hydroformylation. More preferably, the reaction of the rhodium or the rhodium compound takes place in the presence of carbon monoxide and hydrogen at a pressure of from 0.1 to 10 MPa and at a temperature of from 50 to 200° C. Even more preferable are 100 to 150° C. and 1 to 5 MPa, which assure an optimum reaction.

The preparation of the rhodium reaction product is generally carried out in the presence of rhodium-complexing compounds, generally in the presence of an organophosphorus compound, preferably in the presence of the same organophosphorus compound as is used in the running hydroformylation. In other words, when the rhodium reaction product is used in the homogeneous monophasic hydroformylation, the rhodium salt is generally reacted in the presence of water-insoluble phosphines, for example alkyl- or arylphosphines, e.g. triphenylphosphine. When the rhodium reaction product is used in the biphasic liquid—liquid hydroformylation in the presence of an aqueous phase, the preparation of the rhodium reaction product takes place in the presence of the water-soluble phosphines known per se, in particular TPPTS.

The ratio of rhodium to the phosphine in preparing the rhodium reaction product to be added supplementarily in both cases, expressed as the ratio of phosphorus(III) to rhodium, is preferably from 5:1 to 100:1, more preferably from 10:1 to 30:1.

Since the preparation of the rhodium reaction product to be added supplementarily generally employs the same organophosphorus compounds, in particular the same phosphines, as in the running hydroformylation, the preferred organophosphorus compounds are those mentioned above in discussing the hydroformylation process. Therefore, water-insoluble alkyl- or arylphosphines, such as triphenylphosphine, are in particular preferred for the homogeneous monophasic hydroformylation, while water-soluble sulfo-containing phosphines, in particular TPPTS (trisodium triphenylphosphinetrisulfonate), are preferred for the biphasic hydroformylation in the presence of an aqueous phase.

When the reaction product used in accordance with the invention is used in the biphasic hydroformylation, the reaction product is advantageously provided in an aqueous phase which comprises water-soluble phosphine. The preparation of an aqueous solution of the reaction product may in principle be carried out in two different ways, depending on whether the starting material is a water-soluble rhodium compound or a water-insoluble rhodium compound. In a preferred embodiment, rhodium acetate is the water-soluble rhodium starting compound and is reacted with the $CO/H_2$ mixture in an aqueous phase in the presence of a water-soluble phosphine, in particular TPPTS. However, it is also possible to react an organic solution of a water-insoluble rhodium compound, such as rhodium(II) 2-ethylhexanoate with the $CO/H_2$ mixture in the presence of an aqueous phase which comprises the water-soluble phosphine, in particular TPPTS. The rhodium in this processing method is transferred as a water-soluble complex to the aqueous phase, which is then added to the hydroformylation reactor.

Examples of useful organic solvents include aliphatic, cycloaliphatic or aromatic hydrocarbons. There are no particular requirements upon the physical properties of the hydrocarbons. However, they must be free of any impurities which deactivate the catalytically active rhodium. The concentration of rhodium in the hydrocarbon is not critical. It is advantageous to use solutions of average concentration, in particular those comprising at least 3000 mg of rhodium per liter of solution. It is not necessary to use unitary hydrocarbons. Mixtures of different hydrocarbons are also suitable as solvents for the rhodium salts. Useful examples include pentane, hexane, benzine fractions of crude oil, toluene and xylenes.

When an aqueous solution of a water-soluble rhodium salt is converted, the concentration of the rhodium in the aqueous phase is likewise not critical. It is convenient to try to use relatively high concentrations of rhodium, so that at least 3000 mg of rhodium per liter of aqueous solution are obtainable.

The preparation of the rhodium reaction product, depending on the reaction conditions, takes from about 0.5 to 10, usually from 4 to 8 hours.

After the end of the reaction, i.e. pretreatment, the resulting reaction product is generally added directly to the hydroformylation reactor without further workup.

The invention further relates to the use of a reaction product based on rhodium which is prepared by reacting metallic rhodium and/or one or more rhodium compounds in the presence of rhodium-complexing compounds with carbon monoxide and hydrogen for increasing the activity of a catalyst based on rhodium in a catalytic process, preferably a hydroformylation process, which comprises adding said reaction product to said catalytic process. The details of this use may be obtained from the preceding remarks.

Finally, the invention also relates to a process for preparing a catalytic composition, which comprises adding a reaction product based on rhodium to a catalyst based on rhodium from a catalytic process, or preferably a hydroformylation process, to a component comprising the catalyst based on rhodium from to the catalytic process, wherein said reaction product is prepared by reacting metallic rhodium and/or one or more rhodium compounds in the presence of rhodium-complexing compounds with carbon monoxide and hydrogen. The details of the process may be obtained from the preceding remarks.

The following examples illustrate the invention without restricting it to the described embodiments.

Experimental Part

To describe the effectiveness of each catalyst solution, the quantities "activity" and "productivity" were calculated, which are defined as follows:

activity: mol (n+i) of aldehyde/g atom of rhodium×minute productivity: kg (n+i) of aldehyde/liter of catalyst solution×hour The experiments described below were carried out using an aqueous, TPPTS-containing catalyst solution from the operational process (biphasic process) and this was used as a standard for all three experiments.

EXAMPLE 1

Comparative Experiment Using an Aqueous, TPPTS-Containing Catalyst Solution from the Operational Process To obtain the blank level, the catalyst solution without any further additions was placed in a batchwise operated experimental autoclave which was operated as follows. A 0.2 l stainless steel autoclave fitted with a stirrer was charged with propylene and a $CO/H_2$ mixture consisting of equal volumes in such an amount that 10 l/h (STP, 1 liter at STP is equal to 1 liter at a technical pressure of 1 atm and a temperature of 20° C.) of off-gas were withdrawn from the reactor. Simultaneously, 300 ml of aqueous catalyst solution per hour were circulated through the reactor. The hydroformylations were carried out over plural days, and the autoclave was operated for 8 hours per day. The remaining reaction parameters are shown in table 1. The results of the blank test are likewise shown in the following table.

TABLE 1

Propylene hydroformylation by the biphasic process without subsequent supplementary addition of rhodium.

| Experimental duration [h] | 8 | 16 | 32 | 64 |
| --- | --- | --- | --- | --- |
| Temperature [° C.] | 130 | 130 | 130 | 130 |
| Pressure [MPa] | 5 | 5 | 5 | 5 |
| Rh content [mg/kg] | 271 | 271 | 270 | 269 |
| P(III) content [mmol/kg] | 170 | 170 | 169 | 167 |
| Ligand/Rh | 65 | 65 | 65 | 65 |
| C3 quantity [g/h] | 40 | 40 | 40 | 40 |
| Activity [molC4-al/molRh * min] | 14.33 | 14.13 | 14.45 | 14.56 |
| Productivity [kg C4-al/l cat.sol. * h] | 0.213 | 0.210 | 0.215 | 0.216 |
| n/i ratio | 92/8 | 92/8 | 92/8 | 92/8 |

EXAMPLE 2

Addition of 30 ppm of Rhodium Acetate to the Catalyst Solution from the Operational Process Tested in Example 1.

The supplementary addition of 30 ppm of rhodium acetate to the catalyst solution used in example 1 was carried out under similar catalysis conditions. After determining the blank level, supplementary addition was carried out once. The supplementary addition of the rhodium was carried out through the catalyst circulation during the hydroformylation. The hydroformylations were carried out over plural days, and the autoclave was operated for 8 hours per day. The remaining reaction parameters are shown in table 2. The result of the blank test is likewise shown in the following table. This result is comparable with the results from example 1.

TABLE 2

Propylene hydroformylation by the biphasic process with subsequent, non-preformed rhodium addition.

| Experimental duration [h] | Blank test | 8 After addition of 30 ppm of Rh acetate | 16 | 32 | 64 |
| --- | --- | --- | --- | --- | --- |
| Temperature [° C.] | 130 | 130 | 130 | 130 | 130 |
| Pressure [MPa] | 5 | 5 | 5 | 5 | 5 |
| Rh content [mg/kg] | 271 | 300 | 299 | 301 | 300 |
| P(III) content [mmol/kg] | 170 | 170 | 171 | 171 | 169 |
| Ligand/Rh | 65 | 58 | 59 | 59 | 58 |
| C3 quantity [g/h] | 40 | 40 | 40 | 40 | 40 |
| Activity [molC4-al/molRh * min] | 14.20 | 15.13 | 15.01 | 15.29 | 15.18 |
| Productivity [kg C4-al/l cat.sol. * h] | 0.211 | 0.225 | 0.221 | 0.229 | 0.226 |
| n/i ratio | 92/8 | 92/8 | 92/8 | 92/8 | 92/8 |

EXAMPLE 3

Addition of 30 ppm of Preformed Rhodium to the Catalyst Solution from the Operational Process Tested in Example 1.

The supplementary addition of 30 ppm of preformed rhodium to the catalyst solution used in example 1 was carried out under similar catalysis conditions. After determining the blank level, supplementary addition was carried out once. To this end, a solution of 61 mmol of TPPTS and 6.1 mmol of rhodium acetate in 138 g of water, which corresponded to an aqueous catalyst quantity of 140 g, were charged to a 150 ml autoclave in a preceding step. This solution was preformed at 120° C. and 5 MPa of synthesis gas pressure (composition $H_2:CO=1:1$) for 3 hours. The supplementary addition was then carried out by adding 2.1 g of the preformed solution during the hydroformylation through the catalyst circulation. The hydroformylations were carried out over plural days, and the autoclave was operated for 8 hours per day. The remaining reaction parameters are shown in table 3. The result of the blank test is likewise shown in the following table. This is comparable with the results from example 1.

TABLE 3

Propylene hydroformylation by the biphasic process with subsequent preformed rhodium addition.

| Experimental duration [h] | Blank test | 8 After addition of 30 ppm of preformed rhodium | 16 | 32 | 64 |
|---|---|---|---|---|---|
| Temperature [° C.] | 130 | 130 | 130 | 130 | 130 |
| Pressure [MPa] | 5 | 5 | 5 | 5 | 5 |
| Rh content [mg/kg] | 271 | 300 | 299 | 301 | 300 |
| P(III) content [mmol/k] | 170 | 173 | 174 | 173 | 174 |
| Ligand/Rh | 65 | 59 | 60 | 59 | 59 |
| C3 quantity [g/h] | 40 | 40 | 40 | 40 | 40 |
| Activity [molC4-al/molRh * min] | 14.17 | 16.58 | 16.75 | 16.70 | 16.64 |
| Productivity [kg C4-al/l cat.sol. * h] | 0.210 | 0.246 | 0.251 | 0.250 | 0.249 |
| n/i ratio | 92/8 | 92/8 | 92/8 | 92/8 | 92/8 |

As examples 1 to 3 show, subsequent rhodium addition in preformed form allows the activity and productivity of the catalyst system to be clearly improved compared to a rhodium addition in non-preformed form.

What is claimed is:

1. In a process for preparing aldehydes by reaction of olefinically unsaturated compounds with carbon monoxide and hydrogen at temperatures of from 20 to 200° C. and pressures form 0.1 to 50 Mpa in the liquid phase in the presence of a catalyst based on rhodium, the improvement comprising that during the process, supplementary rhodium is added in the form of a reaction product prepared by reacting metallic rhodium and/or one or more rhodium compounds in the presence of rhodium-complexing compounds with carbon monoxide and hydrogen.

2. The process as claimed in claim 1 wherein the reaction of the olefinically unsaturated compounds is carried out in the presence of a liquid aqueous and a liquid organic phase.

3. The process as claimed in claim 1 wherein the reaction of the olefinically unsaturated compounds is carried out in the presence of organophosphorus compounds or their salts.

4. The process as claimed in claim 1 wherein the preparation of said reaction product is carried out at a pressure of from 0.1 to 10 MPa and at a temperature of from 50 to 200° C.

5. The process as claimed in claim 1 wherein said reaction product is prepared by reacting one or more rhodium salts with carbon monoxide and hydrogen.

6. The process as claimed in claim 1 wherein said reaction product is prepared by reacting one or more rhodium salts of an organic compound with carbon monoxide and hydrogen.

7. The process as claimed in claim 1 wherein said reaction product is prepared by reacting one or more rhodium salts of an organic compound selected from the group of rhodium salts consisting of rhodium(III) salts of beta-diketones and rhodium salts of carboxylic acids, with carbon monoxide and hydrogen.

8. The process as claimed in claim 1 wherein said reaction product is prepared by reacting one or more rhodium salts selected from the group of rhodium salts consisting of rhodium(III) acetylacetonate and rhodium salts of aliphatic monocarboxylic acids having from 2 to 18 carbon atoms, with carbon monoxide and hydrogen.

9. The process as claimed in claim 1 wherein said reaction product is prepared by reacting rhodium 2-ethyl hexanoate or rhodium acetate with carbon monoxide and hydrogen.

10. The process as claimed in claim 1 wherein the rhodium-complexing compounds present in preparing said reaction product are organophosphorus compounds or their salts.

11. In a process for preparing a catalytic composition comprising adding a reaction product based on rhodium to a catalyst based on rhodium from a catalytic process or to a component comprising the catalyst based on rhodium from the catalytic process, wherein the improvement comprising said reaction product is prepared by reacting metallic rhodium and/or at least one rhodium compound in the presence of rhodium-complexing compounds with carbon monoxide and hydrogen.

* * * * *